(12) United States Patent
Yamaguchi

(10) Patent No.: US 6,744,507 B2
(45) Date of Patent: Jun. 1, 2004

(54) DRY PARTICLE DISTRIBUTION MEASURING APPARATUS AND METHOD

(75) Inventor: Tetsuji Yamaguchi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 10/316,555

(22) Filed: Dec. 11, 2002

(65) Prior Publication Data

US 2003/0133111 A1 Jul. 17, 2003

(30) Foreign Application Priority Data

Dec. 12, 2001 (JP) .................................. P. 2001-379029

(51) Int. Cl.⁷ .............................................. G01N 15/02
(52) U.S. Cl. ...................................................... 356/336
(58) Field of Search ................................ 356/335–343; 250/208.4, 222.2, 577; 73/865.5; 324/71.4; 702/29

(56) References Cited

U.S. PATENT DOCUMENTS

| 4,708,485 | A | 11/1987 | Illy |
| 5,579,107 | A | 11/1996 | Wright et al. |
| 5,682,235 | A | 10/1997 | Igushi |
| 6,384,128 | B1 * | 5/2002 | Wadahara et al. ........... 524/496 |
| 6,511,712 | B1 * | 1/2003 | Poliniak et al. ............. 427/466 |
| 6,553,849 | B1 * | 4/2003 | Scofield et al. ............ 73/865.5 |

OTHER PUBLICATIONS

"Feeder System for Particle–Size Analyzer" NTIS Tech Notes, U.S. Dept. of Commerce Sep. 1, 1990, p. 743.

* cited by examiner

*Primary Examiner*—Tu T. Nguyen

(57) ABSTRACT

A dry particle-size distribution measuring apparatus and method is applied to powdery and particulate samples that are conventionally known as having a dispersion limit of 1 μm and are dispersed to a state of fine particles or a submicron particle size, and which therefore can be accurately measured. The sample is subjected to primary dispersion by a primary dispersion flow that reaches a critical pressure and a subsonic speed, and the sample is then subjected to a secondary dispersion by a secondary dispersion flow that is different in direction from the primary dispersion flow and that reaches a critical pressure and a subsonic speed. The dispersed primary size powdery and particulate sample is supplied to a flow cell in which air flows, the flow cell 2 is irradiated with a laser beam 6, and the particle-size distribution of the sample is measured on the basis of a detection output of scattered light and/or diffracted light caused by the sample.

20 Claims, 3 Drawing Sheets

DRY PARTICLE DISTRIBUTION MEASURING APPARATUS AND METHOD

BACKGROUND OF THE INVENTION

1. Field of the Invention

The present invention relates to a dry particle-size distribution measuring apparatus in which so-called powdery and particulate members such as powdery members, particulate members, or a mixture of the members are used as a sample, and which measures the particle-size distribution of the sample while flowing the sample by a carrier gas such as air, and more particularly, to an apparatus and method of dispersing the particulate members into a primary particle status prior to submission to a flow cell.

1. Description of Related Art

Dry particle-size distribution measuring apparatus are widely used for measuring the particle-size distribution of powdery and particulate members which are easily soluble in a liquid, such as granules of a medicine, dehydrated food such as seasoning packets for precooked noodles, dried coating compositions, or coating particles.

Such powdery and particulate members are sometimes aggregated by an electrostatic force, a Van der Waals force, a magnetic force, or the like which acts among the powdery and particulate members even in a dry state, so that the powdery and particulate members are not formed as so-called primary particles in which powdery and particulate members are completely separated from each other, but rather are formed as secondary particles (in each of which several primary particles are aggregated) or tertiary particles (in each of which several secondary particles are aggregated). When such powdery and particulate members including not only primary particles but also secondary and tertiary particles are supplied to a flow cell as a sample and measurement is then conducted while irradiating the sample with light, it is impossible to obtain a true particle-size distribution of the powdery and particulate members.

Therefore, conventional dry particle-size distribution measuring apparatuses have been configured in the following manner to address this problem. When powdery and particulate members to be used as a sample are downwardly supplied from a charging port into a flow cell, compressed air may be injected in the outer periphery of the sample charging port, whereby the sample is dispersed so that secondary and tertiary particles in the sample are dispersed to try and change them to primary particles as far as possible.

In a sample dispersion method in the conventional dry particle-size distribution measuring apparatus, however, it is difficult to completely disperse aggregated or bonded powdery and particulate members to primary particles because dispersion is performed only one time. When a sample of high density is charged, or when so-called submicron powdery and particulate members in which the particle size is smaller than 1 $\mu$m are charged as a sample, particularly, there arises a disadvantage that only dispersion up to 1 $\mu$m which corresponds to the secondary particle state is usually performed.

Thus, there is a need in the prior art to provide an efficient and economical fluidic dispersion unit to disperse particles into substantially their primary particle state.

SUMMARY OF THE INVENTION

The present invention has been designed to resolve the above-mentioned problems.

It is an object of the invention to provide a dry particle-size distribution measuring apparatus in which a powdery and particulate sample that is conventionally known in the field of aerial dispersion to have a dispersion limit of 1 $\mu$m can be dispersed to a state of fine primary particles of a submicron particle size, and which therefore can accurately perform a desired particle-size distribution measurement.

In order to attain this objective, in a dry particle-size distribution measuring apparatus in which a powdery and particulate sample is supplied to a flow cell in which air flows, the flow cell is irradiated with a laser beam, and a particle-size distribution of the sample is measured on the basis of a detection output of scattered light and/or diffracted light caused by the sample, the sample which has not yet been supplied to the flow cell is subjected to a primary dispersion by a primary dispersion flow that reaches a critical pressure and a subsonic speed, and the sample is then subjected to secondary dispersion by a secondary dispersion flow that is different in direction from the primary dispersion flow, and that also reaches a critical pressure and a subsonic speed.

In the dry particle-size distribution measuring apparatus, even when the powdery and particulate members are not completely changed into the primary particle state which is the goal of the dispersion by the primary dispersion performed by the primary dispersion flow, the members are also subjected to a secondary dispersion by the secondary dispersion flow that is different in direction from the primary dispersion flow, whereby the entire powdery and particulate members are changed into the primary particle state.

The secondary dispersion flow may be positioned to have a forward angle with respect to a flow axis along the dropping direction of the sample, or may be perpendicular to a dropping direction axis of the sample. Furthermore, a sheath flow may be formed with respect to a flow of the sample after it has been subjected to the secondary dispersion as it is introduced into a measurement sample cell.

The present invention provides a fluidic dispersion unit having a first conduit or flow path for introducing the particulate or powdery sample along a flow axis towards a sample cell. A second conduit or flow path introduces a first peripheral flowing gas to generate first converging force vectors at an angle to the sample flow axis wherein the contact of the first peripheral flowing gas with the particulate or powdery sample generates a first turbulent zone for dispersing the particulate sample to enable a primary particle status. A third conduit or flow path, positioned downstream of the second conduit or flow path, introduces a second flowing gas to generate second force vectors at an angle to the sample flow axis wherein the contact of the second flowing gas with the particulate or powdery sample generates a second turbulent zone for further dispersing the particulate or powdery sample to enhance the ability to provide a primary particle status.

Finally, a fourth conduit can aspirate air as a sheath flow about the sample as it enters the sample measurement cell to insure a repetitive and reproducible flow condition.

The method of the present invention comprises the steps of introducing a particulate or powdery sample along a flow axis towards a sample cell. A first peripheral flowing gas is directed at a first converging angle to the flow axis to contact the sample and create a first turbulent zone to disperse the sample. A second flowing gas is directed downstream of the first flowing gas to contact the sample and create a second turbulent zone for further dispersing the sample to enhance the creation of a primary particle status prior to entering a flow sample cell. A sheath gas flow can be created about the sample to stabilize the measurement condition of the sample in the sample cell.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved dispersion unit and method for powdery and particulate members (hereinafter collectively "particulate sample").

Figure 1:
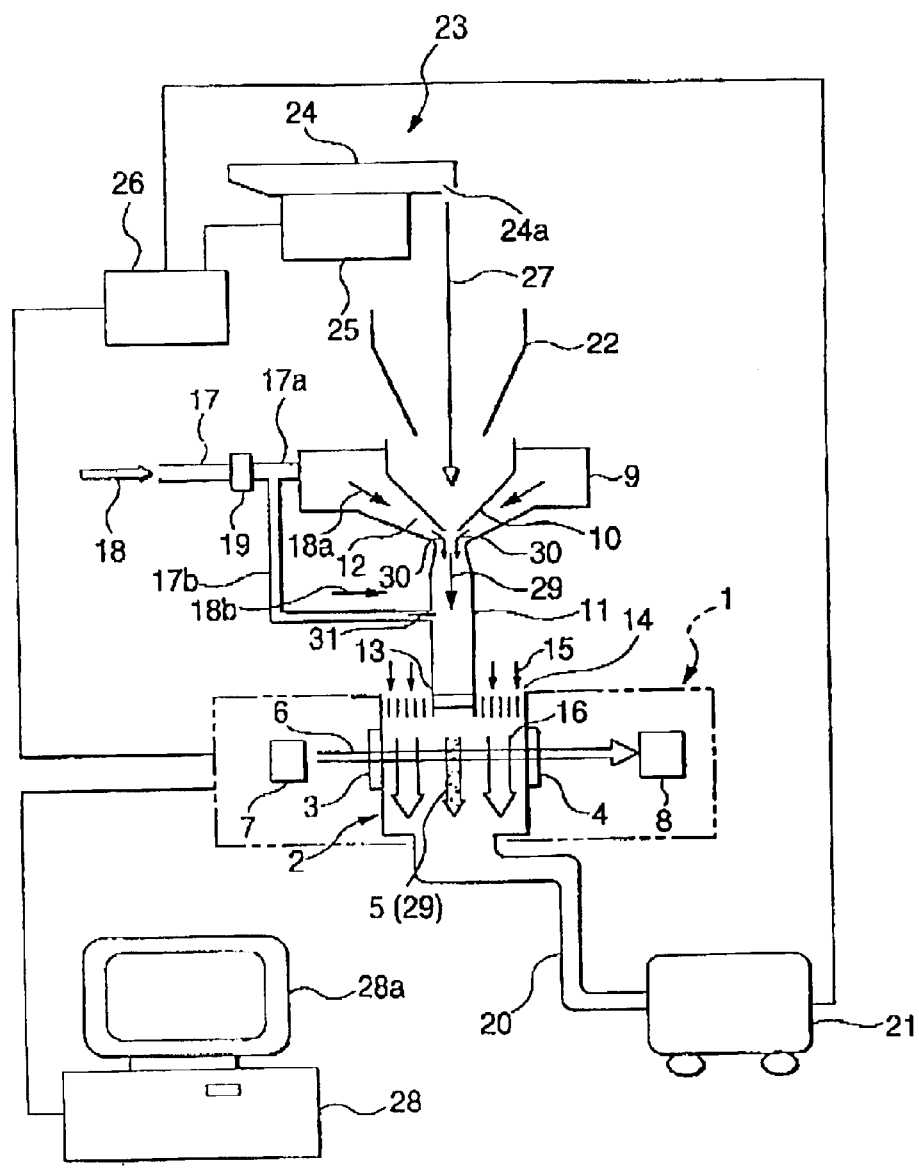
FIG. 1 is a diagram showing a configuration of a dry particle-size distribution measuring apparatus of the present invention.
Figure 2:
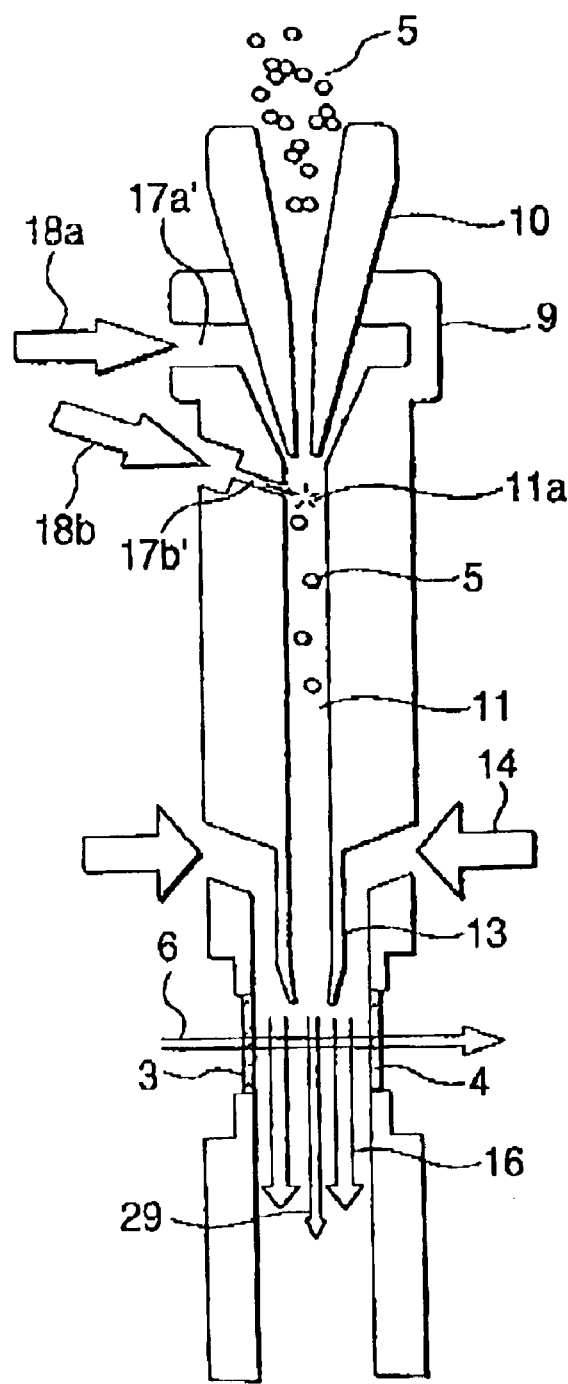
FIG. 2 is an enlarged view of the configuration of main portions of the dry particle-size distribution measuring apparatus of FIG. 1.

Hereinafter, the invention will be described in detail with reference to the Figures. FIGS. 1 and 2 show an embodiment of the present invention. FIG. 1 schematically shows a schematic configuration of the dry particle-size distribution measuring apparatus of the invention, and FIG. 2 shows a configuration of the main portions in an enlarged manner.

In FIG. 1, a measuring section 1 is configured in the following manner. A tubular cell or measurement sample cell 2 is vertically disposed. Optical windows 3 and 4 are formed in opposed side faces of the flow cell, respectively. A laser light source 7 irradiates a sample of powdery and/or particulate members 5 which have been dropped into the flow cell 2. A laser beam 6 is generated outside one of the optical windows such as the optical window 3 so as to be opposed to the other optical window 4. An optical detecting section 8 receives any scattered light and/or diffracted light that is produced by irradiating the sample 5 with the laser beam 6 that passes through the other optical window 4.

A reference numeral 9 denotes a sample ejector or fluidic dispersion unit which serves as a sample introducing section disposed above the flow sample cell 2, and which comprises a funnel-shaped section 10 or first conduit to provide a flow path for the sample. A sample guiding section 11 which communicates with the flow cell 2 is continuously disposed under the funnel-shaped section 10. A gas flow path 12 which guides compressed gas such as air (described later) into the sample guiding section 11 is formed on the side of the lower face of the funnel-shaped section 10. The sample guiding section 11 is insertedly connected above the flow cell 2.

In a lower end portion of the guiding section, a partitioning section 13 is disposed which extends to the vicinities of the upper ends of the optical windows 3 and 4. The reference numeral 14 denotes straightening guide vanes which are disposed around the portion of the sample guiding section 11 insertedly connected to the flow cell 2, so as to be parallel with the partitioning section 13, and through which the outside air 15 is sucked or aspirated so that a sheath flow 16 is formed in the flow cell 2 by the sucked outside air 15 to provide a reproducible flow condition through the sample cell 2.

Reference numeral 17 denotes a compressed-air supply path through which compressed air 18 of, for example, about 1 to 3 atmospheric pressure is supplied into the ejector 9 and the sample guiding section 11. The upstream side of the flow path is connected to a compressed air source (not shown), and comprises a pressure regulating valve 19 such as a digital valve regulator. The air path forks into two separate flow paths 17a and 17b at a position downstream of the pressure regulating valve 19. The downstream end of one of the compressed-air supply paths or the path 17a is communicatingly connected to a side portion of the ejector 9, and that of the other compressed-air supply path 17b is communicatingly connected to a side portion of the sample guiding section 11. Both the paths are configured so as to respectively supply compressed airs 18a and 18b into the ejector 9 and the sample guiding section 11.

In the embodiment, as shown in FIG. 2, the compressed air 18a supplied into the ejector 9 is horizontally blown into the ejector 9 from a blow hole or nozzle 17a at the extreme downstream end of the compressed-air supply path 17a, so as to be perpendicular to the dropping direction or flow axis of the sample 5 which is dropped into the ejector 9. By contrast, the compressed air 18b supplied into the sample guiding section 11 is obliquely downward blown into the sample guiding section 11 from a blow hole or nozzle 17b at the extreme downstream end of the compressed-air supply path 17b, so as to form a forward angle with respect to the dropping direction or axis of the sample 5. Particularly, the position of the blow hole 17b' is set so that the compressed air 18b can be blown to the sample 5 at a position where the dispersion force vectors which are exerted on the sample 5 by the compressed air 18a is maximum, i.e., at the point where the outer peripheral flow due to the compressed air 18a is also converged. The flow speed of the compressed air approaches 331 m/sec.

The reference numeral 20 denotes a sample recovery flow path which is formed on the lower end side of the flow cell 2, and which comprises a suction apparatus 21. The reference numeral 22 denotes a hopper which is disposed above the ejector 9, and which is used for guiding the sample 5 dropped from a sample supplying section (described below), into the ejector 9. The sample 5 can be powder particles of less than 1 $\mu$m in diameter.

The reference numeral 23 denotes the sample supplying section which is disposed above the hopper 22, and which is configured by, for example, a trough 24 and a linear feeder 25. The linear feeder 25 which is controlled by a controller 26 vibrates. The vibration is transmitted to the trough 24 to cause the sample 5 placed on the upper face of the trough to drop along a flow axis as indicated by the arrow 27 from a sample drop hole 24a which is formed in one end of the trough 24.

The reference numeral 28 denotes a calculation and control section which is configured by, for example, a personal computer, and which controls the entire apparatus. Furthermore, the calculation and control section has functions of calculating the particle-size distribution of the sample 5 on the basis of an output signal from the measuring section 1 and by using an arithmetic expression according to Fraunhofer analytic theory or Mie scattering theory, displaying a result of the calculation and the like on a displaying device 28a, and storing the calculation result and the like into a memory section which is disposed in the apparatus, or a memory card or a memory disc which is detachably attached to the apparatus.

In the thus configured dry particle-size distribution measuring apparatus, first, the flow cell 2 is irradiated with the laser beam 6 emitted from the laser light source 7 in a state where the sample 5 is not supplied to the flow cell 2, and a so-called blank measurement is conducted to measure the intensity of light incident on the optical detecting section 8 at this time, thereby obtaining a blank value for establishing a reference value.

After the blank measurement, a measurement of particle sizes of the sample 5 is started. First, the suction apparatus 21 is operated, and the compressed air 18 of a predetermined pressure is flown through the compressed-air supply path 17. Part of the compressed air 18 is blown as the compressed air 18a into the fluidic dispersion unit or ejector 9 via the first compressed-air supply path 17a, and the other part of the compressed air is blown as compressed air 18b into the sample guiding section 11 via the second compressed-air supply path 17b.

In the sample guiding section 11, an air flow 29 caused by the suction apparatus 21 is produced, and the outer peripheral flow (primary dispersion flow) 30 due to the compressed air 18a and reaching a critical pressure and a subsonic speed is produced around and concentrically about the air flow 29 to generate force vectors at a first turbulent zone. When, under this state, the sample 5 configured by dry powdery and particulate members is dropped from the sample supplying section 23 as indicated by the flow axis arrow 27, turbulence is generated by the difference between the converging primary dispersion flow 30 and the flow of the sample 5, along the flow axis 27, whereby the sample 5 is subjected to primary dispersion. The term "critical pressure" is a pressure required to reach a speed of 331 m/sec. The term "subsonic speed" is a speed approximately equal to but not to exceed 331 m/sec. Sound wave speed (Cs) in air is represented by a formula Cs=331+0.6 t where t is temperature.

In the primary dispersion of the sample 5, the powdery and particulate members contained therein which have not yet reached a primary particle state remain in the secondary particle state. At the point 11a where the first outer peripheral flow 30 is converged and the dispersion force is maximum, therefore, the sample 5 which has been subjected to the primary dispersion is subjected to a secondary dispersion by a lateral impulse flow (secondary dispersion flow) 31 caused by the compressed air 18b which is blown through a nozzle in a pinpointed manner into the sample guiding section 11 via the compressed-air supply path 17b. The compressed air 18b also reaches a critical pressure and a subsonic speed, and has a forward angle with respect to the dropping direction of the sample 5. Powdery and particulate members which fail to be changed into the primary particle state even after the initial primary dispersion are, for purposes of sampling, completely dispersed to a primary particle state by the secondary dispersion. Therefore, before supply of the sample 5 to the flow cell 2, the sample 5 is in a primary particle state.

The sample 5 which has undergone two dispersion processes, i.e., the primary dispersion and the secondary dispersion will fall into the flow cell 2 which is disposed at the lower side of the fluidic dispersion unit 9, while maintaining a primary particle state. A sheath gas will surround the sample as it enters the flow cell 2. The falling sample 5 is irradiated with the laser beam 6, whereby scattered light and diffracted light are produced. The second conduit path 17a can include an annular plenum with a plurality of nozzle openings.

The scattered light and the diffracted light are detected by the optical detecting section 8. The optical detecting section 8 outputs a scattered/diffracted light intensity signal corresponding to the particle size. The signal is supplied to the personal computer 28 serving as a calculation and control device. The personal computer 28 calculates the particle-size distribution by using an arithmetic expression according to the Fraunhofer analytic theory or Mie scattering theory, to obtain the particle-size distribution of the sample 5. The measurement result is displayed on the displaying device 28a of the personal computer 28, and stored into, for example, the memory of the personal computer 28. The sample 5 which has undergone the measurement is collected into the suction apparatus 21.

As described above, in the dry particle-size distribution measuring apparatus of the invention, the sample 5 which has not yet been supplied to the flow cell 2 is subjected to primary dispersion by the vertical primary dispersion flow 30 that reaches a critical pressure and a subsonic speed, and the sample 5 which has been subjected to the primary dispersion is then subsequently subjected to secondary dispersion by the secondary dispersion flow 31 that is different (in this example, horizontal) in direction from the primary dispersion flow 30, and that also reaches a critical pressure and a subsonic speed. Even when the sample 5 which is to be measured is not in initially a complete primary particle state, the sample can be dispersed twice by the dispersion flows 30 and 31 after passing through the ejector 9, whereby all of the powdery and particulate members are changed to the primary particle state, so that a desired measurement can be accurately performed. Consequently, a powdery and particulate sample that is conventionally known as common knowledge in the field of aerial dispersion to have a dispersion limit of 1 μm can be dispersed to a state of fine particles or a submicron particle size.

Figure 3:
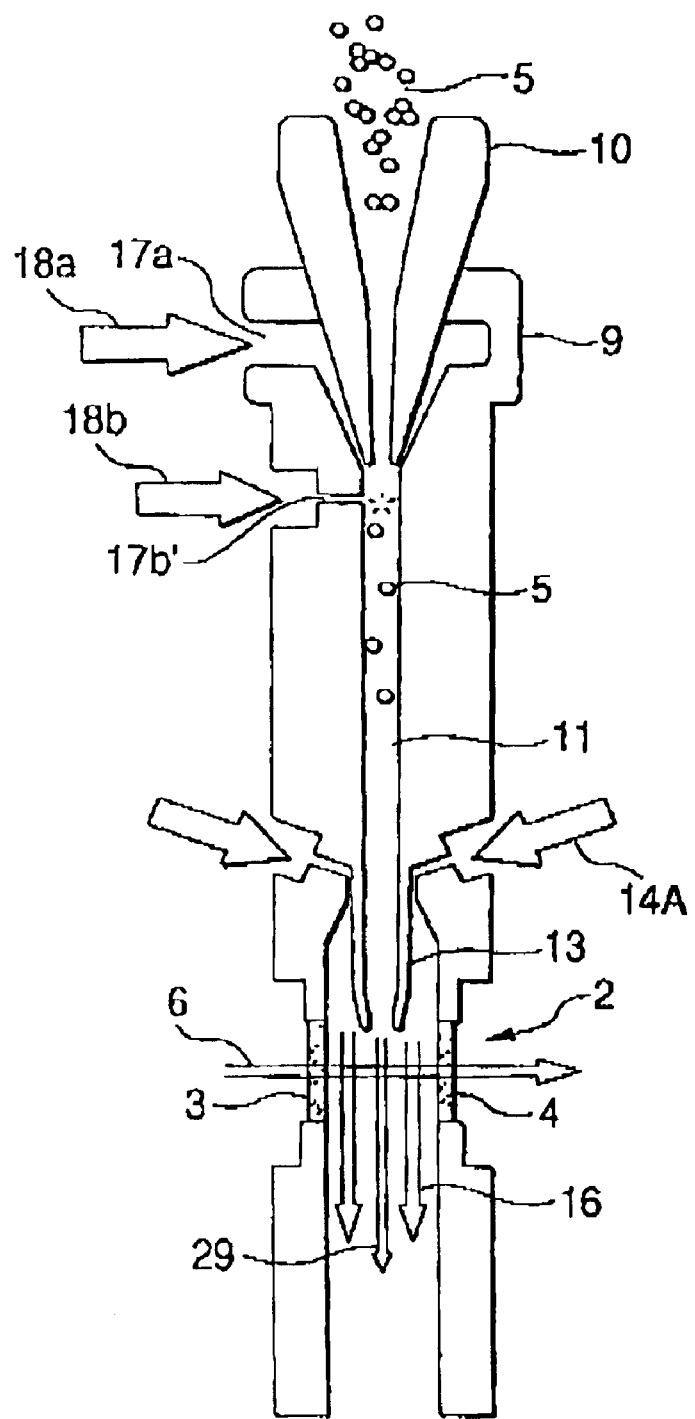
FIG. 3 is an enlarged view of another example of a configuration of the main portions of the dry particle-size distribution measuring apparatus.

In the embodiment described above, the secondary dispersion flow 31 acting on the sample 5 is set so as to form a forward angle with respect to the dropping direction of the sample 5. Alternatively, as shown in FIG. 3, the secondary dispersion flow may be directed perpendicularly to the dropping direction, i.e., horizontally into the sample guiding section 11. In the case where the sheath flow 16 is formed with respect to the flow of the sample 5 which has been subjected to the secondary dispersion, atmospheric air 15 may be used as a source of the sheath flow as in the first embodiment. The flow area for the sheath air flow surrounding the funnel section 10 can have an inner diameter of 7.5 mm and an outer diameter of 7.85 mm, as an example only. Alternatively, as shown in FIG. 3, compressed air 14A, or another gas such as nitrogen, may be used as the source.

The blow hole 17b for the compressed air 18b which is used for producing the secondary dispersion flow 31, and which reaches a critical pressure and a subsonic speed may be further formed in each of a plurality of positions surrounding the converging point 11a of the outer peripheral flow 30 in the sample guiding section 11 and for example can have a diameter of 2 mm.

According to the particle-size distribution measuring apparatus and method of the present invention, in a dry particle-size distribution measuring apparatus in which a powdery and particulate sample is supplied to a flow cell in which a gas flows, the flow cell is irradiated with a laser beam, and the particle-size distribution of the sample is measured on the basis of a detection output of scattered light and/or diffracted light caused by the sample. The sample, prior to being supplied to the flow cell, is subjected to a primary dispersion by a primary dispersion flow that reaches a critical pressure and a subsonic speed, and the sample is then subjected to a secondary dispersion by a secondary dispersion flow that is different in direction from the primary dispersion flow, and that reaches a critical pressure and a subsonic speed. Therefore, a powdery and particulate sample that is conventionally known in this field of aerial dispersion to have a dispersion limit of 1 μm can be dispersed to a state of fine particles or a submicron particle size, and which therefore can accurately perform a desired particle-size distribution measurement.

Those skilled in the art will appreciate that various adaptions and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a dry particle-size distribution measuring apparatus in which a powdery and particulate sample is supplied to a flow cell in which air flows, said flow cell is irradiated with a laser beam, and a particle-size distribution of the sample is measured on the basis of a detection output of scattered light and/or diffracted light caused by the sample, wherein the sample has not yet been supplied to the flow cell, the improvement of:

a primary dispersion member for providing dispersion by a primary dispersion flow that reaches a critical pressure and a subsonic speed, and the sample is subjected to the primary dispersion flow; and a secondary dispersion member for providing dispersion by a secondary dispersion flow that is different in direction from the primary dispersion flow, and that reaches a critical pressure and a subsonic speed wherein the powdery and particulate sample is dispersed into primary sizes prior to introduction into the flow cell.

2. A dry particle-size distribution measuring apparatus according to claim 1, wherein the secondary dispersion flow has a forward angle with respect to a flow axis of the sample.

3. A dry particle-size distribution measuring apparatus according to claim 2, further including a sheath flow unit for directing the dispersed sample into a sheath flow path as it enters the flow cell.

4. A dry particle-size distribution measuring apparatus according to claim 1, wherein the secondary dispersion flow is perpendicular to a flow axis of the sample.

5. A dry particle-size distribution measuring apparatus according to claim 4, further including a sheath flow unit for directing the dispersed sample into a sheath flow path as it enters the flow cell.

6. A dry particle-size distribution measuring apparatus according to claim 1, further including a sheath flow unit for directing the dispersed sample into a sheath flow path as it enters the flow cell.

7. In a dry particle-size distribution measuring apparatus for measuring a particulate sample introduced into a measurement flow cell, the improvement of a fluidic dispersion unit, comprising:

a first conduit for introducing the particulate sample along a flow axis;

a second conduit for introducing a first peripheral flowing gas to generate first converging force vectors at an angle to the first conduit flow axis to generate a first turbulent zone for dispersing the particulate sample to enable a primary particle status; and a third conduit, downstream of the second conduit, for introducing a second flowing gas to generate a second force vector to intersect the converging zone of the first force vectors to provide a secondary dispersion of the particulate sample to further disperse the particles to substantially a primary particle state prior to introduction of the primary particles into the measurement flow cell.

8. The dry particle size measuring apparatus of claim 7, wherein the first conduit is connected to a vibrator unit for receiving the particulate sample.

9. The dry particle-size measuring apparatus of claim 7, wherein the second conduit includes an annular plenum with a plurality of nozzle openings to direct the first peripheral flowing gas to a converging point.

10. The dry particle-size measuring apparatus of claim 9, wherein the third conduit directs the second flowing gas substantially perpendicular to the flow axis.

11. The dry particle-size measuring apparatus of claim 10, wherein the third conduit has a single nozzle opening for directing the second flowing gas.

12. The dry particle-size measuring apparatus of claim 11, further including a fourth annular conduit for providing an aspirated third gas flow surrounding the flow axis of the first conduit into the measurement flow cell.

13. A method of dispersing dry particulate samples prior to introduction into a measurement flow cell, comprising the steps of:

introducing the particulate sample along a flow axis;

directing a first peripheral flowing gas to generate first converging force vectors at an angle to the flow axis to generate a first turbulent zone for dispersing the particulate sample to enable a primary particle status; and directing a second flowing gas to generate a second force vector to intersect a converging zone of the first force vectors to provide a secondary dispersion of the particulate sample to further disperse the particles to substantially a primary particle state prior to introduction of the primary particles into the measurement flow cell.

14. The method of dispersing dry particulate samples according to claim 13, further including directing a third flowing gas to sheath the dispersed particulate sample as it passes through the measurement flow cell.

15. A dry particle-size distribution measuring apparatus for measuring a particulate sample comprising:

a carrier gas source for carrying the particulate sample through the apparatus;

a first conduit for introducing the particulate sample along a flow axis;

a second conduit for introducing a first peripheral flowing gas to generate first converging force vectors at an angle to the first conduit flow axis to generate a first turbulent zone to disperse the particulate sample to enable a primary particle status;

a third conduit, downstream of the second conduit, for introducing a second flowing gas to generate a second force vector to intersect the converging zone of the first force vectors to provide a secondary dispersion of the particulate sample to further disperse the particles to substantially a primary particle state;

a measurement flow cell for receiving the dispersed primary particle state sample;

a measurement unit for irradiating the measurement flow cell and detecting the scattered light and/or diffracted light and providing corresponding output signals, and a control unit for processing the output signals to measure the particle size distribution in the particulate sample.

16. The dry particle-size distribution apparatus of claim 15, further including:

a sheath flow unit for directing the dispersed particulate sample into a sheath flow path as it enters the measurement flow cell.

17. The dry particle-size measuring apparatus of claim 16, wherein the first conduit is connected to a vibrator unit for receiving the particulate sample.

18. The dry particle-size measuring apparatus of claim 17, wherein the second conduit includes an annular plenum with a plurality of nozzle openings to direct the first peripheral flowing gas to a converging point.

19. The dry particle-size measuring apparatus of claim 18, wherein the third conduit directs the second flowing gas substantially perpendicular to the flow axis.

20. The dry particle-size measuring apparatus of claim 15, further including a fourth annular conduit for providing an aspirated third gas flow surrounding the flow axis of the first conduit into the measurement flow cell.

* * * * *